(12) United States Patent
Benson et al.

(10) Patent No.: US 11,628,142 B2
(45) Date of Patent: *Apr. 18, 2023

(54) SINGLE SERVE BEVERAGE POD CONTAINING CANNABIS

(71) Applicants: CannTrust Inc., Vaughan (CA); Single Dose Solutions Inc., Etobicoke (CA)

(72) Inventors: Ronald Stuart Benson, Toronto (CA); Peter Hobbes, Oakville (CA); Claudio Gemmiti, Toronto (CA); Ilana Deborah Platt, Toronto (CA)

(73) Assignees: CannTrust Inc., Vaughan (CA); Single Dose Solutions Inc., Toronto (CA)

( * ) Notice: Subject to any disclaimer, the term of this patent is extended or adjusted under 35 U.S.C. 154(b) by 322 days.

This patent is subject to a terminal disclaimer.

(21) Appl. No.: 16/944,750

(22) Filed: Jul. 31, 2020

(65) Prior Publication Data

US 2020/0375896 A1 Dec. 3, 2020

Related U.S. Application Data

(60) Division of application No. 15/286,960, filed on Oct. 6, 2016, now Pat. No. 10,758,481, which is a continuation of application No. 14/731,675, filed on Jun. 5, 2015, now Pat. No. 9,480,647.

(60) Provisional application No. 62/008,853, filed on Jun. 6, 2014.

(51) Int. Cl.
| | |
|---|---|
| *A61K 9/00* | (2006.01) |
| *A61J 1/14* | (2006.01) |
| *B65B 29/02* | (2006.01) |
| *A23L 2/52* | (2006.01) |
| *A23L 2/39* | (2006.01) |
| *A61J 1/00* | (2006.01) |
| *A61K 36/185* | (2006.01) |
| *B65B 7/28* | (2006.01) |
| *B65D 85/804* | (2006.01) |

(52) U.S. Cl.
CPC .............. *A61K 9/0095* (2013.01); *A23L 2/39* (2013.01); *A23L 2/52* (2013.01); *A61J 1/00* (2013.01); *A61J 1/1443* (2013.01); *A61K 36/185* (2013.01); *B65B 7/2842* (2013.01); *B65B 29/022* (2017.08); *B65D 85/8043* (2013.01); *B65D 85/8046* (2013.01); *A61K 2236/00* (2013.01); *A61K 2236/10* (2013.01); *A61K 2236/15* (2013.01)

(58) Field of Classification Search
CPC ... A61J 1/00; A61K 2236/00; A61K 2236/10; A61K 2236/15; A61K 36/185; A61K 9/0095; B65B 29/02; B65B 7/16; B65B 29/022; B65B 7/2842; B65D 85/8043; B65D 85/808; B65D 85/8046; A23L 2/39; A23L 2/52
See application file for complete search history.

(56) References Cited

U.S. PATENT DOCUMENTS

| | | | |
|---|---|---|---|
| 4,279,824 A | 7/1981 | McKinney | |
| 5,325,765 A | 7/1994 | Sylvan | |
| 5,776,537 A | 7/1998 | Blanc | |
| 5,840,189 A | 11/1998 | Sylvan et al. | |
| 6,550,371 B1 | 4/2003 | Del Bon | |
| 7,622,140 B2 | 11/2009 | Whittle et al. | |
| D682,675 S | 5/2013 | Rapparini | |
| 8,445,034 B1 | 5/2013 | Coles | |
| 8,808,734 B2 | 8/2014 | Winnicki | |
| 9,480,647 B2 | 11/2016 | Benson et al. | |
| 10,758,481 B2 * | 9/2020 | Benson ..................... | A23L 2/52 |
| 2003/0017216 A1 | 1/2003 | Schmidt et al. | |
| 2004/0033280 A1 | 2/2004 | Whittle | |
| 2004/0147767 A1 | 7/2004 | Whittle et al. | |
| 2005/0042172 A1 | 2/2005 | Whittle | |
| 2010/0012118 A1 | 1/2010 | Storz | |
| 2010/0035978 A1 | 2/2010 | Guy et al. | |
| 2012/0021075 A1 | 1/2012 | Umanskaya et al. | |
| 2012/0043242 A1 | 2/2012 | Hospodor | |
| 2012/0046351 A1 | 2/2012 | Hospodor | |
| 2012/0061263 A1 | 3/2012 | Sibley | |
| 2012/0095087 A1 | 4/2012 | Hyatt | |
| 2012/0121764 A1 | 5/2012 | Lai | |
| 2012/0269933 A1 | 10/2012 | Rapparini | |
| 2013/0295172 A1 | 11/2013 | Freeman | |
| 2015/0136158 A1 | 5/2015 | Stevens et al. | |

(Continued)

FOREIGN PATENT DOCUMENTS

| | | |
|---|---|---|
| CA | 2503310 | 10/2006 |
| CN | 101904393 | 7/2010 |

(Continued)

OTHER PUBLICATIONS

Nuensinger, A "Amped-up Drinks . . . " GQ, Culture: The GQ Guide to Outdoor Parties, Jun. 28, 2013, <URL: gq.com/story/best-drinks-for-barbecues> accessed online Aug. 12, 2022, 11 pages. (Year: 2013).*
PCT International Searching Authority International Search Report and Written Opinion relating to application No. PCT/CA2015/050522, dated Jul. 30, 2015.
Website document entitled "House of Jane—Jane's Brew: Medicinal Gourmet Coffees, Tea and Fine Edibles". 2014. 8-pages. Downloaded from http://www.houseofjane.com/.
Grasscity Forums website posting entitled "Can i put wee in a Keurig machine to make coffee?". Posted online to this website forum by Brody on Jan. 2, 2013. 16-pages. http://forum.grasscity.com/incredible-edible-herb/1157132-can-i-put-wee-keurig-machine . . . .

(Continued)

*Primary Examiner* — Aaron J Kosar
(74) *Attorney, Agent, or Firm* — Rowand LLP (57) ABSTRACT

Single-serve containers for use in brewing a *cannabis*-based beverage are described, as are methods for preparing a single-serve container configured for receipt in a single-serve brewing machine. The method includes: adding a processed *cannabis* product to the single-serve container; adding, to the single-serve container, at least one of an extraction or flavoring agent; and sealing the single-serve container.

12 Claims, 8 Drawing Sheets

(56) References Cited

U.S. PATENT DOCUMENTS

2015/0155502 A1    6/2015   Ishibashi et al.
2015/0352044 A1    12/2015   Benson et al.
2017/0020814 A1    1/2017   Benson et al.

FOREIGN PATENT DOCUMENTS

| | | |
|---|---|---|
| CN | 102845568 | 6/2011 |
| EP | 1757361 | 2/2007 |
| EP | 2490962 | 4/2011 |
| WO | 9958035 | 11/1999 |
| WO | 2015192230 | 12/2015 |

OTHER PUBLICATIONS

Website document entitled "How to make cann-oil" Tips and tricks from Kitchen Kush. Feb. 3, 2014. 3-pages. http://www.thecannabist.co/2014/02/03/kitchen-kush-making-canna-oils-recipe/3451/.
Website document entitled "Fructus Cannabis". 3-pages. Aug. 22, 2015 from http://www.tcmwiki.com/wiki/fructus-cannabis.
AU Examination report dated Nov. 24, 2017.
CA Office Action dated Feb. 17, 2017.
CA Office Action dated Apr. 20, 2016.
European Supplementary Search Report dated Jan. 11, 2018.

* cited by examiner

SINGLE SERVE BEVERAGE POD CONTAINING CANNABIS

The present application is a divisional of U.S. application Ser. No. 15/286,960 filed Oct. 6, 2016 which is a continuation of U.S. application Ser. No. 14/731,675 filed Jun. 5, 2015, which is a non-provisional application of U.S. Application Ser. No. 62/008,853 filed Jun. 6, 2014. The contents of these applications are incorporated herein by reference.

TECHNICAL FIELD

The present application relates to *cannabis* and, more particularly, to *cannabis* products such as single-serve beverage pods containing *cannabis* and methods of preparing *cannabis* products such as single-serve beverage pods.

BACKGROUND

*Cannabis*, which is commonly known as marijuana, is often used as a medicine for the treatment of a variety of conditions. *Cannabis* contains numerous cannabinoids, such as delta-9-tetrahydrocannabinolic Acid (THCA). Acidic cannabinoids, such as THCA and cannabidiolic acid (CBDA) may be converted to more active cannabinoids, through a process known as decarboxylation. For example, THCA is converted to delta-9-tetrahydrocannabinol (THC) through decarboxylation.

Decarboxylation is typically performed by smoking *cannabis*. The heat generated during smoking decarboxylates the inactive cannabinoids, such as THCA, into the active form, such as THC.

The use of smoking as a means for delivering the active ingredients in *cannabis* to a patient has a number of problems. For example, ensuring a proper dosage for medical marijuana users is difficult with smoking since each patient has different smoking tendencies which will affect the dose. More particularly, medical marijuana is often prescribed as a dose per day by weight for a patient. An example of a medical marijuana prescription may be 0.5 g of marijuana taken two times per day for a period of 30 days. Different users may, however, inhale a different amount of the active ingredients when smoking. For example, the actual dose for a patient (i.e. the amount actually consumed) will depend on variables such as the elapsed time between inhales, the amount of time that the patient holds the smoke in, the tightness of the *cannabis* cigarette, the moisture content of the cigarette (which may affect the burn rate between breaths) and other variables.

Also, some patients may be reluctant to smoke marijuana because of a stigma associated with smoking marijuana, perceived health concerns associated with smoking, or their inability to smoke effectively due to other medical conditions.

Thus, there is a need for improved methods of delivering medical marijuana.

BRIEF DESCRIPTION OF THE DRAWINGS

Reference will now be made, by way of example, to the accompanying drawings which show embodiments of the present application, and in which.

Like reference numerals are used in the drawings to denote like elements and features.

DETAILED DESCRIPTION OF EXAMPLE EMBODIMENTS

In an aspect, the present application describes a method of preparing a single-serve container configured for receipt in a single-serve brewing machine. The method includes: adding a processed *cannabis* product to the single-serve container; adding, to the single-serve container, at least one of an extraction or flavoring agent; and sealing the single-serve container.

In another aspect, a single-serve container for use with a single-serve brewing machine is described. The single-serve container includes a body portion having an open end and a membrane covering the open end of the body portion. The membrane and the body portion define a cavity. A processed *cannabis* product is located within the cavity. At least one of an extraction agent or flavoring agent is located within the cavity.

In yet another aspect, a method of preparing *cannabis* for rapid extraction using water is described. The method includes packaging *cannabis* and an extraction agent together to form a packaged beverage product.

In at least some embodiments, the method of preparing *cannabis* further includes decarboxylating the *cannabis*. In at least some such embodiment, the *cannabis* packaged with the extraction agent is the decarboxylated *cannabis*.

In yet another aspect, a packaged beverage product is described. The packaged beverage product includes a container. The packaged beverage product includes *cannabis* and an extraction agent in a cavity defined by the container.

In at least some embodiments, the *cannabis* included in the packaged beverage product is decarboxylated and/or pulverized *cannabis*.

In yet another aspect, a method of preparing *cannabis* for rapid extraction using water is described. The method includes: pulverizing the *cannabis*; filtering the *cannabis* by passing at least a portion of the pulverized *cannabis* through a sieve; and retaining the portion of the pulverized *cannabis* that passed through the sieve.

In another aspect, the present application describes a method of preparing *cannabis* for rapid extraction using water. The method includes: decarboxylating the *cannabis*; adding the decarboxylated *cannabis* and an extraction agent into a single-serve container, the single-serve container configured for receipt in a brewing machine; and sealing the single-serve container.

In another aspect, a method of preparing *cannabis* for rapid extraction using water is described. The method includes: pulverizing the *cannabis* to a particle size of 2 millimeters or less; adding the pulverized *cannabis* and an extraction agent into a single-serve container, the single-serve container configured for receipt in a brewing machine; and sealing the single-serve container.

In another aspect, a method of preparing a single-serve container is described. The method includes: adding powdered chocolate into the single-serve container, the single-serve container configured for receipt in a brewing machine; adding *cannabis* into the single-serve container; and sealing the single-serve container containing the *cannabis* and the powered chocolate and no other extraction agent apart from the powdered chocolate.

In another embodiment, a single-serve container for use with a single-serve brewing machine, is described. The single-serve container includes a body portion having an open end and a membrane covering the open end of the body portion. The membrane and the body portion define a cavity. The container also includes *cannabis* located within the cavity and an extraction agent located within the cavity. In at least some embodiments, the *cannabis* in the container is decarboxylated and/or pulverized *cannabis*.

As will be described in greater detail below, in some embodiments, a method is described for delivering THC and other active components of marijuana using existing single-serve beverage machines, such as single-serve brewing machines. Single-serve brewing machines are machines that receive single-serve containers having specific dimensions, shapes or features. The single-serve containers are often called pods. The brewing machines may, for example, be Keurig™ brewing machines (or Keurig™ compatible brewing machines) which are configured to receive a K-cup™ or a K-cup compatible pod. By way of further example, the brewing machines may be Tassimo™ brewing machines and may be configured to receive a T Disc™ or T-disc compatible pods. Other types of brewing machines are also contemplated.

The brewer (which is also referred to as a brewing machine herein) may be configured to pierce the pod with one or more spray nozzle(s) which passes water into the pod. More specifically, the nozzle may be pointed at its end, to allow the nozzle to easily pierce the pod. By piercing the pod, an inlet is created which allows water to flow into the pod (e.g. through the nozzle).

In some embodiments, such as embodiments in which a hard-shell container is used, the brewer may also pierce the pod a second time to create a hole for discharge of a brewed beverage. That is, an outlet is created through which the brewed beverage may exit the pod (e.g. into a cup).

As will be described in greater detail below, a single-serve container is provided which includes *cannabis* so that the brewed beverage includes cannabinoids. Accordingly, in some embodiments, a single-serve container is described which delivers cannabinoids using a Keurig™ coffee brewer, a Tassimo™ coffee brewer, or a single-serve brewer of another type.

Example Container

Figure 1:
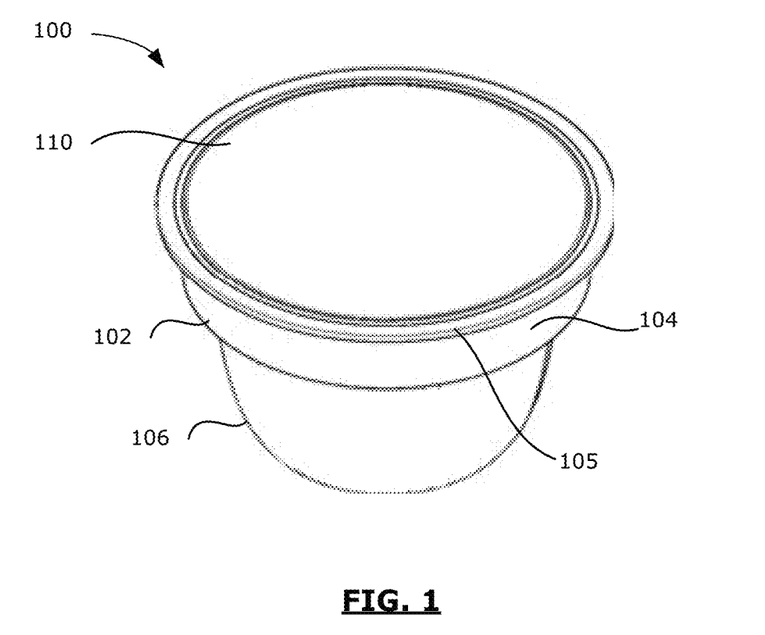
FIG. 1 is a top perspective view of a soft-shell single-serve container according to an embodiment of the present disclosure.
Figure 2:
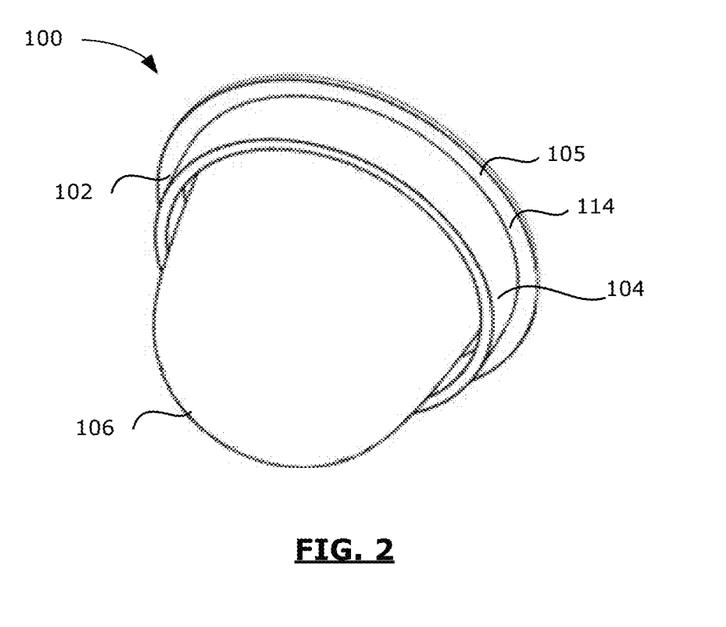
FIG. 2 is a bottom perspective view of the soft-shell single-serve container of FIG. 1.
Figure 3:
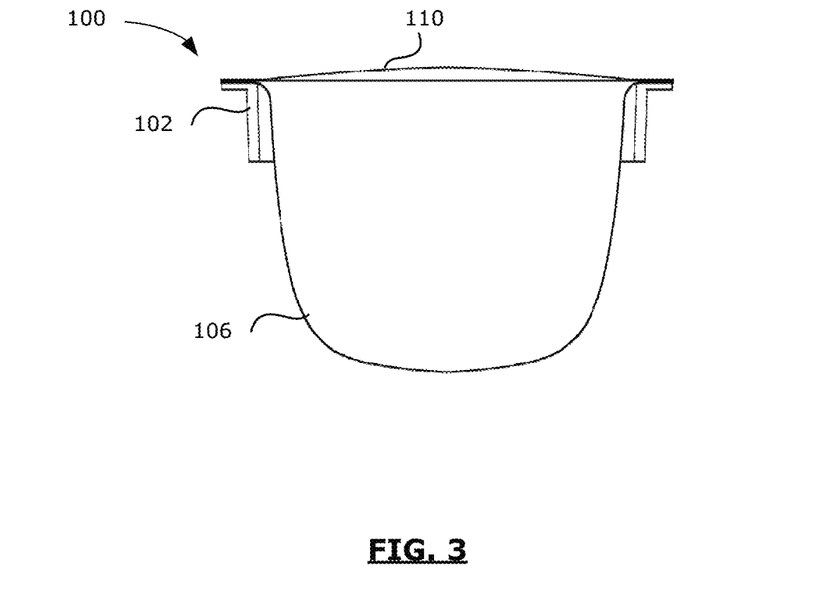
FIG. 3 is a cross-sectional view of the single-serve container of FIG. 1.

Referring first to FIGS. 1 to 3, an example single-serve container 100 is illustrated. FIG. 1 illustrates the container using a top perspective view, FIG. 2 illustrates the container using a bottom perspective view, and FIG. 3 illustrates the container using a cross sectional view.

In the example illustrated, the single-serve container 100 is constructed of three principal components—a body portion 106, a support ring 102, and a membrane 110. The body portion 106 acts as an exterior shell for the single-serve container and also acts as a filter. This style of container may be referred to as a soft-shell container.

The support ring 102 is constructed of a rigid material, such as a rigid plastic, and functions to maintain the shape of the container 100. The support ring 102 also acts as a support for the container 100 when the container is inserted within a brewing machine of the type described above. More particularly, the brewing machine includes a cartridge seat (which may also be referred to as a cartridge holder) which receives the container 100. The support ring 102 contacts the cartridge seat of the brewing machine and holds the container 100 in position for a brew cycle. The diameter of the support ring 102 is sized based on the cartridge seat.

The support ring 102 includes a vertical wall portion 104 and a horizontal portion 105 connected to the vertical wall portion 104. The horizontal portion 105 is the portion that is in the same plane as a top opening of the body portion 106. The horizontal portion 105 provides an upper flat surface which is configured for receiving a membrane 110, which seals the container 100, and a lower flat surface 114 which contacts the cartridge seat of the brewing machine.

The vertical wall portion 104 provides additional rigidity to the support ring and to the container generally. The vertical wall portion 104 may be generally cylindrical in some embodiments. In some such embodiments, the support ring 102 has an L-shaped cross section. However, the vertical wall portion 104 may not be cylindrical in all embodiments and may, for example, be a sloped surface which forms an angle with an axis extending along the center of the support ring 102. For example, the vertical wall portion 104 may form the shape of a truncated cone having two open ends. The vertical wall can take on many different shapes and configurations without significantly affecting the functionality of the pod.

The support ring 102 connects with the body portion 106 of the container 100. For example, during construction of the container 100, the support ring 102 may be heat-sealed to the body portion 106. By way of further example, the support ring 102 may be connected to the body portion 102 with a welding process such as ultrasonic bonding or adhesive. The body portion 106 is generally shaped as an open cup or pail.

The body portion 106 is constructed of a filtering material, such as a mesh. The filtering material is permeable to allow a liquid beverage to pass through the body portion 106. However, the filtering material is fine enough to prevent any non-soluble solid contents of a particular size (such as tea, *cannabis* or coffee grinds) in the container 100 from passing through the body portion 106.

In at least some embodiments, the body portion 106 is thermoformed from a flat textile or film. The body portion 106 may, for example, be thermoformed using one or more techniques described in U.S. publication number 20120269933 A1, filed Oct. 19, 2010 by Gino Rapparini, the contents of which are hereby incorporated by reference.

The body portion 106 is generally thermoformed into the shape of a cup or a pail, to form an interior space for receiving *cannabis* or a processed *cannabis* product (such as *cannabis* processed according to a method described below), and, in at least some embodiments, a food-based extraction agent (which is described in greater detail below) and, in at least some embodiments, a flavoring agent such as tea, coffee or chocolate flavoring, such as cocoa powder.

The body portion 106 may also include a rim portion at the open end, which is flat and which sits on the horizontal portion 106 of the support ring 102. The rim portion may be heat sealed to the support ring 102 or attached to the support ring using another technique such as ultrasonic bonding or an adhesive.

A membrane 110 seals the container 100. More particularly, the membrane 110 is attached at the open end of the body portion 106 to seal the body portion 106 and provide a cover to the body portion 106. The membrane 110 and the body portion 106 collectively define a cavity which stores the processed *cannabis* product (or *cannabis*), food based extraction agent and, in some embodiments, one or more flavoring agents.

The membrane 110 may be a barrier film membrane, which is substantially impermeable to liquids and/or gases. The membrane 110 is thin and rigid, when applied to the container 100, to allow a needle of the brewer to pierce the membrane and extend into the cavity defined by the membrane 110 and the body portion 106 to expel water into the cavity.

In at least some embodiments, the height of the container 100 (i.e. the distance between the membrane 110 and the bottom of the body portion 106) is in the range of 10 to 30 mm and the volume of the cavity is in the range of 15 to 40 mL. In at least some embodiments, the height of the container 100 is in the range of 15 to 35 mm.

The membrane 110 may be attached to other portions of the container 100 after the contents of the pod have been placed into the interior space defined by the body portion 106. The membrane 110 may be attached by heat sealing or ultrasonic welding. For example, in at least some embodiments, the membrane may be attached to a body portion of the container.

The single-serve container illustrated in FIGS. 1 to 3 requires the container to be pierced by only a single needle at a single side. More particularly, when used in a brewing machine, the container 100 is pierced at its top (i.e. through the membrane 110) using a needle. During brewing, the needle injects water into the container 100, which passes through the permeable body portion 106, flows through one or more exit ports in a brewing chamber of the brewing machine (the brewing chamber is the portion of the brewing machine that receives the container 100) and drips into a pot, cup, or other receptacle. This needle may be referred to as a nozzle. In this embodiment, because the pod is defined by a permeable filter, which acts as a housing for the pod, there is no need to puncture the bottom of the pod in order to extract the brewed liquid.

The single-serve container 100 may be configured to be used in available brewing machines, such as a Keurig™ brewing machine.

Figure 4:
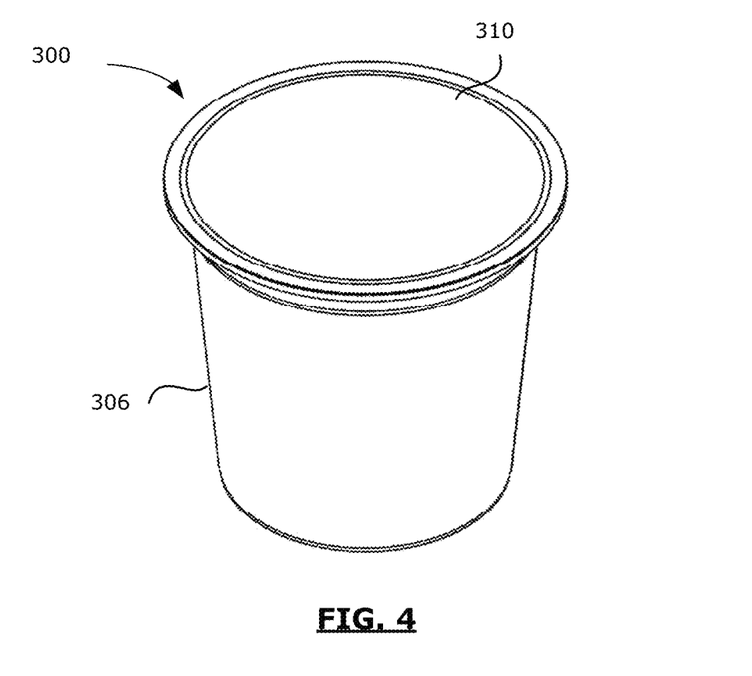
FIG. 4 is a perspective view of an example hard-shell single-serve container according to an embodiment of the present disclosure.

The single serve container may, in other embodiments, take other forms. By way of example, in some embodiments, the single serve container 100 may be a hard shell container. An example hard shell single-serve container 300 is illustrated in FIGS. 4 and 5.

Figure 5:
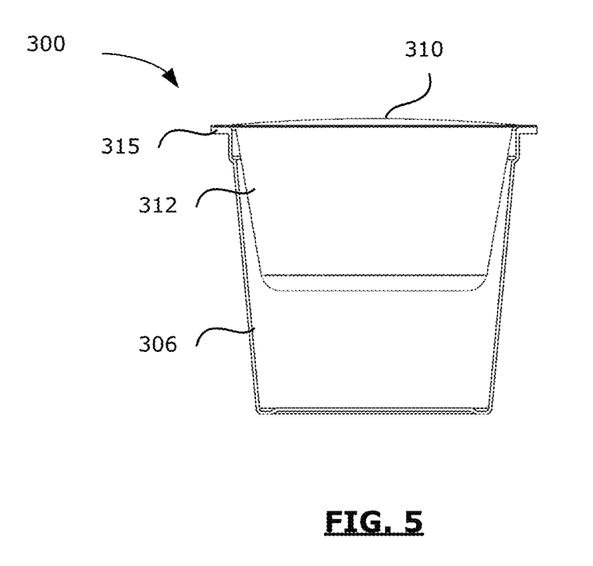
FIG. 5 is a cross-sectional view of the single-serve container of FIG. 4.

The hard shell single-serve container 300 is constructed of three principal components—a body portion 306, a membrane 310, and a filter 312 (illustrated in FIG. 5).

The body portion 306 is constructed of a non-permeable (to water or oxygen) material. The body portion 306 is, in at least some embodiments, piercable by an outlet needle associated with a brewing machine. Piercing the body portion 306 creates an outlet which allows a brewed beverage to exit the container 300 during brewing.

In the example illustrated, the body portion 306 has a truncated conical shape. More specifically, the body portion 306 is shaped like a bucket or pail, having a closed bottom end and an open top end. The body portion 306 may have other shapes in other embodiments. For example, in some embodiments, the body portion 306 may be cylindrical.

The body portion 306 performs many of the same functions as the support ring 102 of the embodiment of FIG. 1. For example, the body portion 306 generally maintains the shape of the container 300 and acts as a support for the container 300 when the container 300 is inserted within a brewing machine of the type described above. That is, the container 300 may be placed in a cartridge seat. The body portion 306 may include a ring 315 portion which contacts the cartridge seat of the brewing machine and holds the container 300 in place.

In the embodiment illustrated, the body portion 306 acts as a housing but not a filter. Instead, a filter 312 (illustrated in FIG. 5) is disposed within an interior space defined by the body portion 306 (i.e. the cavity between the membrane 310 and the body portion 306). As can be seen from the sectional view of FIG. 5, the filter 312 may also have a truncated conical shape, having a top open end and a bottom closed end. In other embodiments, the filter 312 may take other shapes, including a cone.

The filter 312, in the example illustrated, is positioned within a cavity that is defined by the body portion 306 and the membrane 310. The filter 312 is constructed of a permeable material such as a mesh or cloth. In at least some embodiments, the filter may be a nonwoven fabric. Filters 312 may be formed from natural fiber-based material or from a polymer-based material, for example. The filter may, for example, be folded from sheet material or may be stretched from a sheet material. Stretch forming can include thermoforming using heat. The filter 312 is permeable to allow a liquid beverage to pass through the filter, but it is fine enough to prevent any solid contents (such as tea, *cannabis* or coffee grinds) in the container 300 from passing through the filter 312.

In the embodiment illustrated, the top end of the filter 312 is attached to the top end of the body portion 306. This may be done using any of the techniques that are described above for attaching the body portion 106 of the soft-shell container 100 to the support ring 102.

The height of the filter 312 is less than the height of the body portion 306 such that, when the filter 312 is attached to the body portion 306, there is a gap between the filter 312 and the bottom of the body portion 306. This gap allows a drainage needle to pierce the body portion 306 without penetrating the filter 312.

The container 300 is sealed with a membrane 310, which may be of the type described above with reference to the soft-shell container 100. When the membrane 310 is attached to the body portion 306, a first cavity is defined by the membrane 310 and the body portion 306. A second cavity, which is defined by the membrane 310 and the filter 312, is located within the first cavity. The second cavity stores *cannabis* or a processed *cannabis* product (such as decarboxylated and/or pulverized *cannabis*), and, in at least some embodiment, a food-based extraction agent and, in some embodiments, one or more flavoring agents.

The membrane 310 and the body portion 306 may be air-tight. That is, the container 300 may be air-tight. In at least some embodiments, the first cavity defined by the membrane 310 and the body portion 306 may be nitrogen flushed when the membrane 310 is applied to expel oxygen from the cavity and prevent the degradation of the processed *cannabis* product (or *cannabis*), food-based extraction agent and/or flavouring agent (e.g. Coffee).

Accordingly, the single-serve container may take a variety of forms. Generally, the single-serve container includes a membrane and a body portion. The body portion may be permeable and may be used as a filter in some embodiments (as in the case of the embodiment of FIGS. 1 to 3), or there may be a secondary filter (as with FIGS. 4 and 5).

In some embodiments, the single-serve container is a K-cup™ container. K-cup containers are described in greater detail in U.S. Pat. No. 5,840,189, the contents of which are hereby incorporated by reference.

In some embodiments, the single serve container may be a T Disc™ style container which is configured for use with a Tassimo™ brewer. T disc style containers are described in U.S. Pat. No. 7,231,869 which was filed on Jan. 23, 2004 and which is incorporated herein by reference.

In some embodiments, the single serve container may be a Nespresso™ container or Nespresso™ compatible container. In some embodiments, the single serve container may be a Nescafe™ Dolce Gusto™ style container.

The containers may take other forms apart from those listed above but the general mode of action is similar. The single serve pod serves to hold and protect the *cannabis* and other ingredients internally, where the hot water is introduced to extract the actives and then ejected through the brewer head.

Preparation of *Cannabis* for Rapid Extraction using Pre-Decarboxylation

Figure 6:
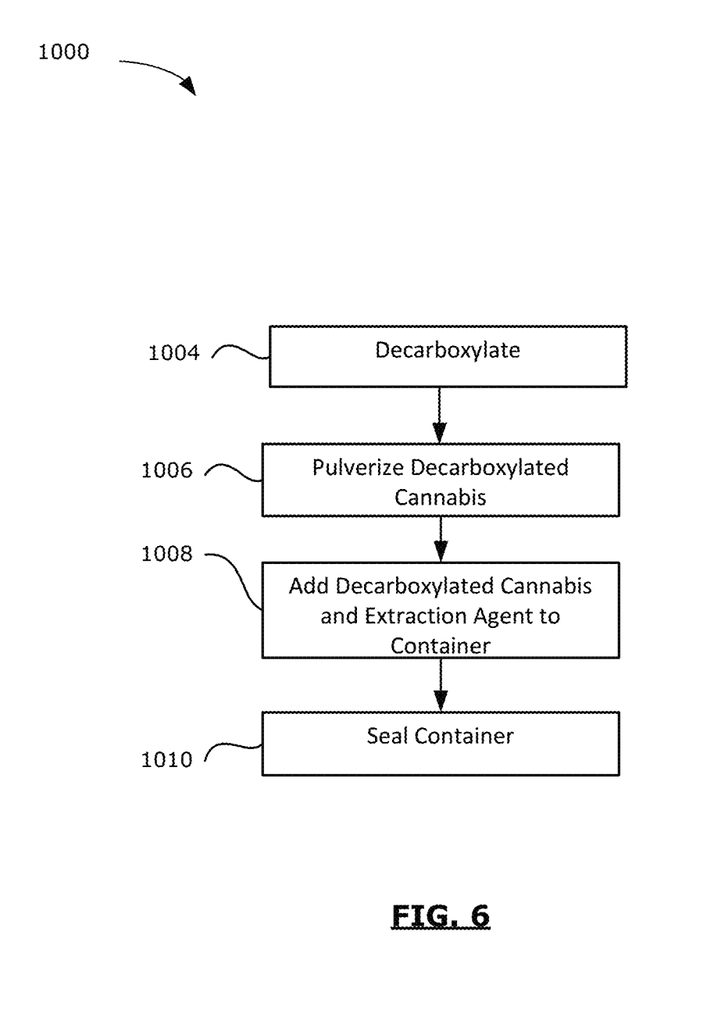
FIG. 6 is a flowchart of a method for facilitating rapid extraction of *cannabis* into a liquid.

Referring now to FIG. 6, a method 1000 of preparing *cannabis* for rapid extraction using water is illustrated. The *cannabis* may be of any strain including pure or hybrid varieties such as *Cannabis sativa* or *Cannabis indica*. While not illustrated in FIG. 6, the *cannabis* may be harvested before or during the performance of the method. The *cannabis* that is used in the method (or in the method 1100 described below with reference to FIG. 7) may include any of the bud, leaves, or fines portions of a *cannabis* plant, or a combination thereof.

At 1004, the *cannabis* may be decarbaroxylated. More particularly, the cannabinoids in the *cannabis* may be decarboxylated. This process of decarboxylating the cannabinoids in the *cannabis* is referred to herein as decarboxylating the *cannabis*. Decarboxylation is the process of removing a carbon dioxide group from a molecule. Decarboxylation converts inactive cannabinoids, such as delta-9-tetrahydrocannabinolic acid (THCA) to active cannabinoids such as delta-9-tetrahydrocannabinol (THC).

The decarboxylation of the *cannabis* occurs by heating the *cannabis*. For example, in some embodiments, the decarboxylation is performed by heating the *cannabis* in an oven (e.g., by baking). The oven may be at a temperature of between 120 degrees Celsius and 140 degrees Celsius and the *cannabis* may be heated for a time period in the range of 30 to 60 minutes. It will be appreciated that the temperature of the oven and the bake time have an inverse relationship. For example, if the oven is at 120 degrees Celsius, then the bake time may be 60 minutes but if the oven is at 140 degrees Celsius, then the bake time may be only 30 minutes. The bake time is sufficiently long to permit decarboxylation, but short enough that the THC does not appreciably convert to cannabinol (CBN).

In an embodiment, the temperature of the oven is selected to be below the boiling point of the cannabinoids, flavonoids, and terpenoids found in *cannabis*. Flavonoids are a class of plant pigments. Terpenoids and Flavonoids are, in part, responsible for the look, taste and odor of a particular strain of *cannabis*. Terpenoids, which are structurally related to terpenes, are naturally occurring in a wide range of plants. In part, they contribute to what gives the plants their unique aromatic quality. Beta-sitosterol is a flavonoid which has a relatively low boiling point of 134 degrees Celsius (as compared with the boiling points of the other flavonoids, cannabinoids and terpenoids commonly found in *cannabis*). Thus, in at least some embodiments, the decarboxylation is performed at a temperature that is less than the boiling point of 134 degrees Celsius. For example, in at least some embodiments, the temperature may be 130 degrees or less.

The oven used in the heating may be a continuous process oven, such as a conveyor oven. A conveyor oven is an oven that is equipped with a conveyor which slowly moves the *cannabis* through a heating chamber at a predetermined speed until it reaches a position where it is expelled from the heating chamber. For example, *cannabis* may be added to the conveyor at an upstream end of the conveyor, which may be located outside the heating chamber. The *cannabis* is then drawn into the heating chamber due to movement of the conveyor and is slowly moved across the length of the heating chamber, where it eventually expelled from the heating chamber at a downstream end of the conveyor.

THC degrades in the presence of oxygen. Accordingly, in some embodiments, the decarboxylation of the *cannabis* may occur under hypoxic or anoxic conditions to prevent exposure of the *cannabis* to oxygen. That is, the oven used to decarboxylate may be air-tight and may contain little oxygen so as to prevent the degradation of the *cannabis*.

Furthermore, since THC degrades in the presence of light, in at least some embodiments, the decarboxylation is performed in a light-free or low-light environment. For example, in some embodiments, the oven is configured to prevent light penetration such that the *cannabis* is shielded from light during the baking. For example, the oven may be constructed of an opaque housing which prevents penetration of light and the oven may not include any windows.

Other methods of heating the *cannabis* to decarboxylate the *cannabis* may be used in other embodiments (i.e. apart from the use of an oven).

At 1006, the decarboxylated *cannabis* is pulverized, or otherwise broken apart into small particles. The pulverizing may be performed by impacting, beating, crushing, rolling, grinding or otherwise applying a force to the *cannabis* to break it apart. The pulverizing may be performed using a pulverizing machine. That is, the *cannabis* is inserted into the pulverizing machine and the pulverizing machine then impacts the *cannabis* to break it apart. For example, the pulverizing machine may be of a type commonly used in the food or drug industries.

In some embodiments, prior to the pulverizing, the *cannabis* is freeze dried in order to facilitate pulverization. The freeze drying may be performed by applying liquid nitrogen (or other freezing liquid or gas) to the *cannabis*. The freeze dried *cannabis* is then inserted into the pulverizing machine and the pulverizing performed. The freeze drying of the *cannabis* may be useful to ensure the pulverized *cannabis* has a powder-like consistency.

Such freeze drying may occur after decarboxylation, in some embodiments. In such embodiments, the freeze drying assists to stop the rapid decarboxylation process by cooling the *cannabis*. Such rapid cooling may be helpful to provide a highly consistent and repeatable decarboxylation process.

Freeze drying may, in some embodiments, be performed prior to decarboxylation. Freeze drying prior to decarboxylation may be useful to reduce the moisture content of the *cannabis* and to reduce the particle size of the *cannabis* for the decarboxylation process. More specifically, once the *cannabis* is freeze dried, it is brittle and has a tendency to break apart. In at least some embodiments, freeze drying prior to pulverization is performed so that the *cannabis* is broken down to a greater extent for the decarboxylation process (in embodiments in which pulverization occurs prior to decarboxylation). A smaller particle size during decarboxylation may assist with decarboxylation and may allow the *cannabis* to be decarboxylated in shorter time periods.

In some embodiments, the pulverizing may occur under hypoxic or anoxic conditions to prevent exposure of the *cannabis* to oxygen. That is, the pulverizing machine may be air tight and may provide a low oxygen environment. Further, in some embodiments, the pulverizing may occur under low-light or no-light conditions, to prevent exposure of the *cannabis* to light. That is, the pulverizing machine may have a light-free pulverizing chamber or region to prevent light from reaching the *cannabis* while in the pulverizing machine.

In other embodiments, the *cannabis* may not be protected from oxygen or light during the pulverizing stage. In some such embodiments, the *cannabis* may be exposed to typical ambient levels of oxygen or light and the pulverizing step may be completed rapidly to ensure that the cannabinoids are not degraded during pulverization. In some embodiments, the pulverizing may be completed within five minutes or less.

The pulverization at 1006 may, in at least some embodiments, yield pulverized *cannabis* with a particle size of two millimeters or less. In some embodiments, the *cannabis* is pulverized to a particle size of 1 millimeter or less. In some embodiments, the *cannabis* is pulverized to a particle size of 0.5 millimeter or less. The fine consistency of the pulverized *cannabis* improves extraction of the cannabinoids into the beverage (e.g., such as water). More particularly, the pulverizing serves to increase the surface area of the *cannabis* which allows for better extraction of the cannabinoids into the beverage.

While not illustrated in FIG. 6, the pulverized *cannabis* may be filtered prior to step 1008 to ensure a desired and uniform particle size. For example, in some embodiments, the pulverized *cannabis* may be passed through one or more sieves. The sieves may be used to remove pulverized *cannabis* particles that are either too big or too small. As noted above, the maximum size for the particles may be set to ensure sufficient surface area of the *cannabis*. The lower size limit, if any, may depend on the filter used in the single-serve container. More particularly, the lower size limit may be set to prevent the particle from passing through the filter of the single-serve container. In at least some embodiments, the particle size of the pulverized *cannabis* is between 0.25 mm and 2 mm That is, the sieve may be configured so that only *cannabis* having such a particle size is used for the following steps of the method 1000 of FIG. 6. Any *cannabis* having a larger particle size may be further pulverized before being further used. In one embodiment, the sieve(s) may be configured such that the *cannabis* having a particle size of 1 mm or less is included in the container at step 1008 (discussed below). In another embodiment, the sieve(s) may be configured such that the *cannabis* having a particle size of 0.5 mm or less is included in the container at step 1008 (discussed below). In one embodiment, only *cannabis* having a particle size between 0.5 mm and 1 mm is added to the container. A small particle size has been found to generally produce a beverage having greater potency.

In the method 1000 of FIG. 6, the pulverizing (at 1006) is illustrated as being performed after the decarboxylating (at 1004). This order of processing eases the handling of material during the decarboxylating step 1004 since the *cannabis* is larger during the decarboxylating step with this ordering and, therefore, is easier to handle. However, in some embodiments, the ordering of these steps may be reversed. In one embodiment, pulverization occurs prior to decarboxylation so that the *cannabis* has a consistent surface area during decarboxylation to produce highly repeatable results.

After the *cannabis* is pulverized, the resulting processed *cannabis* product is added to a single-serve container at 1010. The container may be of any of the types described above including, for example, the type of container 100 described above with reference to FIGS. 1 to 3, the container 300 described with reference to FIGS. 4 and 5, a K-cup, a T Disc™ style container, a Nespresso™ container or Nespresso™ compatible container, a Nescafe™ Dolce Gusto™ style container, or a single-serve container of another type which has a form factor that is configured for receipt within a single-serve beverage dispenser including a single-serve brewing machine such as a single-serve coffee maker.

The processed *cannabis* product (which is, in at least some embodiments, the *cannabis* that has been decarboxylated and pulverized) is added to an interior space of the container (such as a single serve container 100, 300 of the type described above) at 1008. In some embodiments, the *cannabis* may be added to the container using a hopper. In at least some embodiments, the hopper feeds a filling head which dispenses the processed *cannabis* product into the container. For example, in some embodiments, the filling head may be associated with a screw mechanism that pushes a specific amount out of the filling head by way of controlled rotation of the screw. In this way, the amount of processed *cannabis* product added to the container may be strictly controlled.

The amount of processed *cannabis* product added to the container is predetermined and will depend on the desired dosage level for the container. By way of example, the *cannabis* may be added in any one of the following doses: 0.25 grams, 0.5 grams, 0.75 grams, 1.0 gram. It will be appreciated that other doses apart from those defined above may also be used.

The addition of the processed *cannabis* product is performed with strict tolerance controls regarding the quantity of processed *cannabis* product added so that each container receives the desired quantity of *cannabis* within an accepted tolerance level (e.g. 2% in some embodiments). As a result, the THC and CBD levels in each beverage produced using the containers at a given dosage level are highly consistent. By way of example, a patient who repeatedly brews beverages with 0.25 gram dosage containers will ingest a consistent amount of THC and CBD each time the beverage is produced (assuming they use the same brew conditions including length of brew and temperature). Such consistency is not found in smoking or vaporization, which are currently the most common methods of using *cannabis*.

An extraction agent is also added to the container at 1008. Cannabinoids, such as THC, have a low solubility in water and so an extraction agent is used so that the cannabinoids may be efficiently extracted into water. The extraction agent is a lipid-rich food substance. The extraction agent is a food-based extraction agent in that it is capable of being safely consumed by a human. In at least some embodiments, the extraction agent is a substance which is classified as a food and not a food additive. The food-based extraction agent may be a lipid. The food based-extraction agent is, in at least some embodiments, a solid at room temperature and may be selected from a group which includes, but is not limited to, milk powder, coconut flour or flakes, *quinoa* flour, flax meal and almond flour. The particle size of the extraction agent is, in some embodiments, the same or similar (e.g. within 15%) to that of the pulverized *cannabis*. The particle size of the extraction agent may be selected or modified to achieve uniform mixing with other contents of the container (e.g. *cannabis*) and to prevent de-mixing. The food-based extraction agent is, in at least some embodiments, in powder form when it is added to the container at 1008. The powder form may, for example, be useful to ensure that the extraction agent remains in the container's interior space until brewing (e.g. to ensure it does not pass through the container's filter, which is the body portion 106 in the container of FIG. 1).

However, in some embodiments, the extraction agent may be an oil such as, for example, soybean oil, peanut oil, coconut oil, etc. In some embodiments, the extraction agent may be a creamer such as a milk-based creamer (i.e. a dairy creamer) or a non-dairy creamer. Other extraction agents are also possible apart from those specifically recited above.

In some embodiments, during step 1008, the extraction agent and the processed *cannabis* product (e.g., *cannabis* which has been decarboxylated and pulverized) are mixed together to create a mixture and then the mixture is added to the container (e.g. the extraction agent and *cannabis* may be added via a common hopper and filler). In other embodiments, the processed *cannabis* product and extraction agent may be separately added to the container. For example, the processed *cannabis* product may be added to the container using a first hopper and the extraction agent may be added using another hopper.

In at least some embodiments, at least 0.9 grams of fat are provided by the extraction agent added to the container. In some embodiments, the extraction agent provides 0.9 to 2.5 grams of fat. In other embodiments, the fat content may be more or less. For example, in some embodiments, the fat content may be less than 0.5 g.

Other ingredients may also be added to the container during step 1008. For example, in some embodiments, a flavoring agent is added. The flavoring agent may be used to enhance the flavor of the beverage created when the container is used in a single-serve beverage machine. In at least some embodiments, the flavoring agent may provide a beverage that a user might ordinarily consume, even if they were not consuming a *cannabis*-based beverage. That is, the flavoring agent may be a common beverage with a flavor for any common beverage. For example, in some embodiments, the flavoring agent is coffee and, more particularly, is roasted and ground coffee. The ground coffee may be complemented with additional flavoring to enhance the coffee flavor such as, for example, irish cream flavoring, vanilla flavoring, hazelnut flavoring, etc.

In at least some embodiments, the ground coffee has a particle size that ranges between 291 and 570 microns. In at least some embodiments, some grinds may have a larger particle size. For example, in some embodiments, at least 90% of grinds are 570 microns or less.

In some embodiments, the flavoring agent may be tea including, for example, black tea, green tea, white tea, or other teas. The tea may include cured leaves of the tea plant, *Camellia sinesis* and/or may include other ingredients such as fruits or herbs. For example, in some embodiments, the tea may be one of rosehip tea, chamomile tea, or rooibos tea.

In at least some embodiments, the tea has a density of between 95-200 grams per 500 ml. In some embodiments, the maximum moisture of the tea is 12% or less. In some embodiments, the tea has a fanning in the range of 0.2-2.5 mm for the bulk of the sample (e.g. at least 80% of the tea is within this range).

In some embodiments, the flavoring agent may be chocolate which may be provided in powder form. In at least some embodiments, cocoa powder may be used. In some embodiments, the chocolate powder may be made by agglomerating cocoa powder, sugar, milk powder or a non-dairy creamer and other flavours and/or artificial sweeteners. The ingredients may be agglomerated to a specific size and density in order to prevent filtering through the filter (which may be a filter or a permeable body portion of a container), to facilitate dissolution during brewing and to ensure sufficient quantities can be delivered to maximize the sensory impact of the powder.

Since the chocolate powder contains both cocoa fat and milk or non-dairy creamer fats, in some embodiments, the chocolate may serve as both a flavoring agent and an extraction agent. That is, no extraction agent is added to the container apart from the chocolate.

In at least some embodiments, the chocolate powder has a particle size that ranges between 291 and 570 microns. In at least some embodiments, some particles may have a larger particle size. For example, in some embodiments, at least 90% of particles are 570 microns or less.

In some embodiments, the flavoring agent may be a syrup or concentrate such as, for example, a soda-flavored or fruit-flavored syrup or concentrate. By way of example, the syrup may be cola-flavored. By way of further example, in some embodiments, the flavoring agent may be cappuccino or latte. Liquid flavoring agents may not work with all containers described herein or may benefit from modifications to at least some the containers described herein.

The quantity of flavoring agent used will depend on the nature of the flavoring agent used. For example, 6 to 12 grams of coffee may be used. In other embodiments, 9 to 20 grams of coffee may be used. By way of further example, in some embodiments, 4 to 7 grams of tea may be used. In yet other embodiments, 6 to 14 grams may be used. By way of further example, in some embodiments, 6 to 10 grams of chocolate powder may be used. In some embodiments, 8 to 20 grams of chocolate powder may be used.

The flavoring agent may, in some embodiments, be mixed with one or both of the processed *cannabis* product and the extraction agent to create a mixture and then the mixture is added to the container (e.g. the flavoring agent, *cannabis* and, in some cases, the extraction agent may be added via a common hopper or filler).

In some embodiments, the flavoring agent may be added separately from the extraction agent and/or the processed *cannabis* product. For example, in some embodiments, the *cannabis* is added using a first hopper and the flavoring agent is added using a second hopper. In such embodiments, the extraction agent may be added via either the first hopper, the second hopper, or a third hopper.

In some embodiments, the flavoring agent and the processed *cannabis* product are added to a common compartment within the container. That is, the flavoring agent and the *cannabis* may contact one another within the container since there is no physical barrier separating the flavoring agent and the *cannabis* within the container. In other embodiments, the container may be constructed with a physical barrier which separates the interior space of the container into multiple chambers. One of those chambers may store the processed *cannabis* product and the extraction agent while the other may store the flavoring agent.

Furthermore, in some embodiments, an emulsifier is added to the container. The emulsifier may be lecithin, for example. When a beverage is created using the single-serve container, the emulsifier allows the oil droplets containing the cannabinoids to disperse within the beverage to create a more homogeneous and palatable beverage.

At 1010, the single-serve container 100, 300 is sealed. For example, a membrane 110, 310 may be applied to the container 100, 300. The membrane acts as a lid to the container, closing the interior space of the container. The membrane may be configured to be pierced by a nozzle associated with the beverage machine. The membrane is, in some embodiments, applied using heat. In some embodiments, the membrane is applied using induction sealing or ultrasonics.

In some embodiments, such as the embodiment of FIGS. 4 and 5, the membrane provides an air-tight seal for the container 300 so that air cannot enter or exit the container's interior space. In at least some such embodiments, to prevent degradation of the cannabinoids, the oxygen within the interior space is displaced. That is, the oxygen in the vicinity of the decarboxylated *cannabis* may be displaced. This displacement may be performed, for example, by nitrogen flushing the container. That is, the interior space of the container is nitrogen flushed during the application of the membrane so that, once sealed, the container contains only minute amounts of oxygen (e.g., less than 1%).

In other embodiments, the membrane may not provide an air-tight seal. For example, where the container is constructed in the manner illustrated in FIGS. 1 to 3 so that the container's body portion is permeable, the membrane does not provide an air-tight seal. Instead, a non-permeable overwrap may be applied to the single-serve container and the oxygen may be displaced within the overwrap. For example, the overwrap may be vacuum sealed and/or nitrogen flushed. Once sealed, the container 100, 300 (and the *cannabis* inside the container) is only exposed to trace amounts of oxygen (e.g., less than 1%).

In at least some embodiments, the overwrap may be constructed of a thin foil which may be formed and sealed so that it resembles a potato-chip bag or small pillow pack. To prevent degradation of the cannabinoids by light, the overwrap may be opaque.

In the method 1000, the decarboxylation of the *cannabis* may be performed prior to packaging the *cannabis* in a single-serve container (at 1008). This allows the single-serve container to work with existing common brewing machines, which have short brew cycles. For example, in some embodiments, the brewing machine may be configured to brew a cup of coffee in two minute or less and the cannabinoids may be extracted into a hot water beverage within this time frame. In at least some embodiments, the brewing machine is configured to brew a 10 oz beverage, such as a cup of coffee, in one minute or less.

Furthermore, the pre-decarboxylation allows the container to be used to brew either a cold water beverage (such as a soda or fruit juice) or a hot water beverage (such as coffee, tea or hot chocolate, cappuccino, latte).

In at least some embodiments, the method 1000 or a portion thereof may be an automated process.

Preparation of *Cannabis* for Rapid Extraction using Pulverization

In the embodiment described immediately above, decarboxylation was performed prior to packaging the processed *cannabis* product into a single-serve container. As noted above, this allows for cold-water brewing and for brewers having short brewing cycles. However, in other embodiments, the *cannabis* is not pre-decarboxylated. For example, in some embodiments, decarboxylation could be performed after packaging the processed *cannabis* product.

Figure 7:
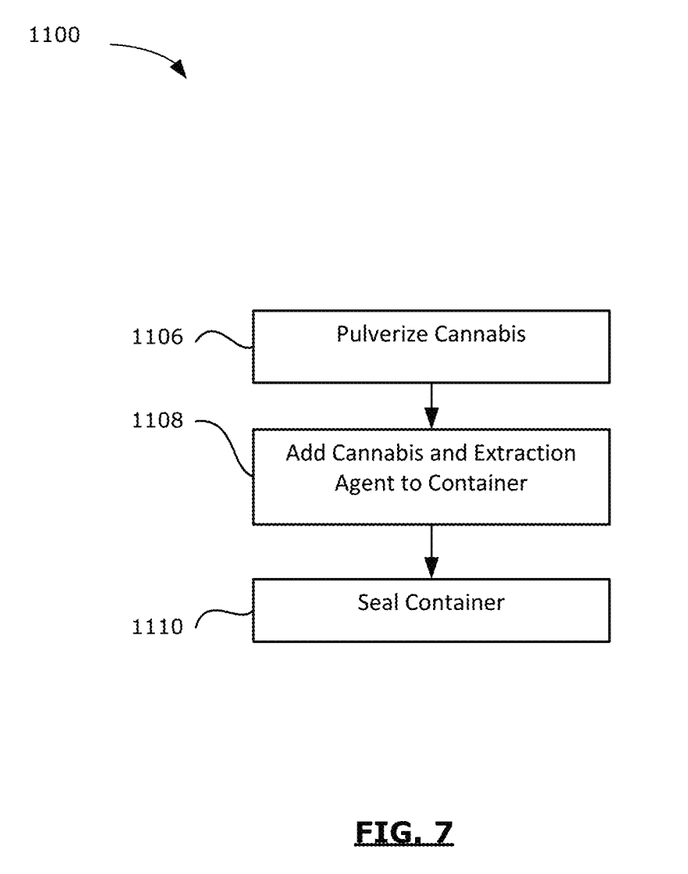
FIG. 7 is a flowchart of a method for facilitating extraction of *cannabis* into a liquid.

Referring now to FIG. 7, a further method 1100 of preparing *cannabis* for rapid extraction is illustrated. In this method 1100, *cannabis* is prepared for rapid extraction by pulverizing the *cannabis* to a small particle size and packaging the pulverized *cannabis*, along with an extraction agent, into a container.

The method 1100 of FIG. 7 includes many steps that are the same or similar to those discussed above with reference to the method 1000 of FIG. 6.

At 1106, the *cannabis* is pulverized. The *cannabis* is pulverized to a small particle size. In at least some embodiments, the *cannabis* may be pulverized to a particle size of 2 millimeters or less. In some embodiments, the *cannabis* may be pulverized to a particle size of 1 millimeter or less. In another embodiment, the *cannabis* may be pulverized to a particle size of 0.5 millimeters or less. In some embodiments, the *cannabis* may be pulverized to a particle size of between 0.5 mm and 1 mm. 1106 may be performed in the same manner as described above for step 1006 of the method 1000 of FIG. 6, except that in the method 1100 of FIG. 7, the *cannabis* is not decarboxylated. For example, the *cannabis* may be freeze-dried prior to pulverizing. The *cannabis* that is pulverized may be fresh *cannabis* in some embodiments and dried *cannabis* in other embodiments. Accordingly, in some embodiments, the method 1100 may include a step of drying the *cannabis*. While some decarboxylation may occur in this stage, the intention of this stage is not to decarboxylate the *cannabis* but rather to dry the *cannabis*. The *cannabis* is, in some embodiments, dried in an oven. For example, in some embodiments, the *cannabis* may be dried in an oven at a temperature of 100 to 105 degrees Celsius for 10 to 20 minutes. In one embodiment, the *cannabis* is dried at 105 degrees Celsius for 15 minutes.

At 1108, the processed *cannabis* product (e.g., the pulverized *cannabis*) and an extraction agent is added to a single-serve container, which may be of the type described herein. The addition of the pulverized *cannabis* and the extraction agent may operate in the same manner as that described above with reference to the step 1008 of the method 1000 of FIG. 6 except that the *cannabis* which is added to the container is not decarboxylated in the method 1100 of FIG. 7. Furthermore, the extraction agent added at 1108 may be of a type described above with reference to step 1008 of the method 1000 of FIG. 6. A flavoring agent of the type described above may also be added in the manner described above.

At 1110, the container is sealed. 1110 may be performed in the manner described above with reference to step 1010 of the method 1000 of FIG. 6.

The method 1100 of FIG. 7 may be automated in at least some embodiments.

Modified Containers for Improved Wetting of *Cannabis*

In at least some embodiments, a single-serve container may be used which is formed to increase the amount of *cannabis* that is wetted directly by a nozzle during the brewing cycle.

Figure 8:
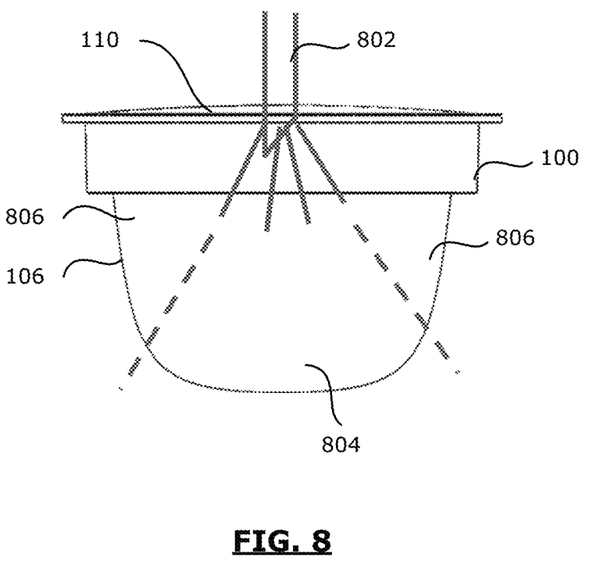
FIG. 8 is a side view of a soft-shell container and a nozzle associated with a brewing machine.

To appreciate how the container may be arranged to provide improved wetting, reference will first be made to FIG. 8, which illustrates the container 100 of FIGS. 1 to 3 in side view. In FIG. 8, a nozzle 802 is also illustrated. The nozzle 802 pierces the membrane 110 and enters the cavity defined by the membrane 110 and the body portion 106. Broken lines are used to demarcate a direct nozzle spray zone 804. The direct nozzle spray zone 804 is the region that the nozzle 802 wets directly. That is the direct nozzle spray zone 804 is the region that is directly within the full pressure spray path of water expelled from the nozzle. The nozzle spray zone 804 is distinct from the nozzle spray periphery zone 806. The nozzle spray periphery zone 806 is a region that is not directly within the full pressure spray path of the water expelled from the nozzle. Ingredients located within the nozzle spray periphery zone 806 may be wetted as the container 100 fills with water, but the ingredients in this portion may not be as wetted, or as forcefully wetted, as the ingredients located within the nozzle spray zone 804. Accordingly, the container may be modified to increase the amount of ingredients located in the nozzle spray zone 804 and decrease the amount of ingredients in the nozzle spray periphery zone 806.

Figure 9:
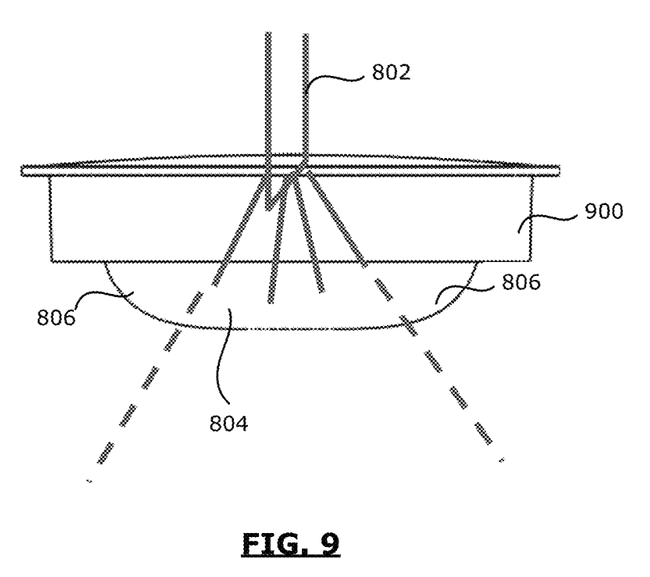
FIG. 9 is a side view of a soft-shell container and a nozzle associated with a brewing machine.

To further illustrate the distinction between these zones, a further embodiment of a container 900 is illustrated in FIG. 9. In this embodiment, the container is a flatter-style container. For example, the width of the container may be 2-3 times the height of the container. In one embodiment, the width of the container is approximately 2.5 times the height of the container. Using this configuration, the amount of ingredients which may be in the nozzle spray periphery zone 806 is relatively large, at least in comparison to the amount of ingredients in this zone in the embodiment described below with reference to FIGS. 10 and 11.

Figure 10:
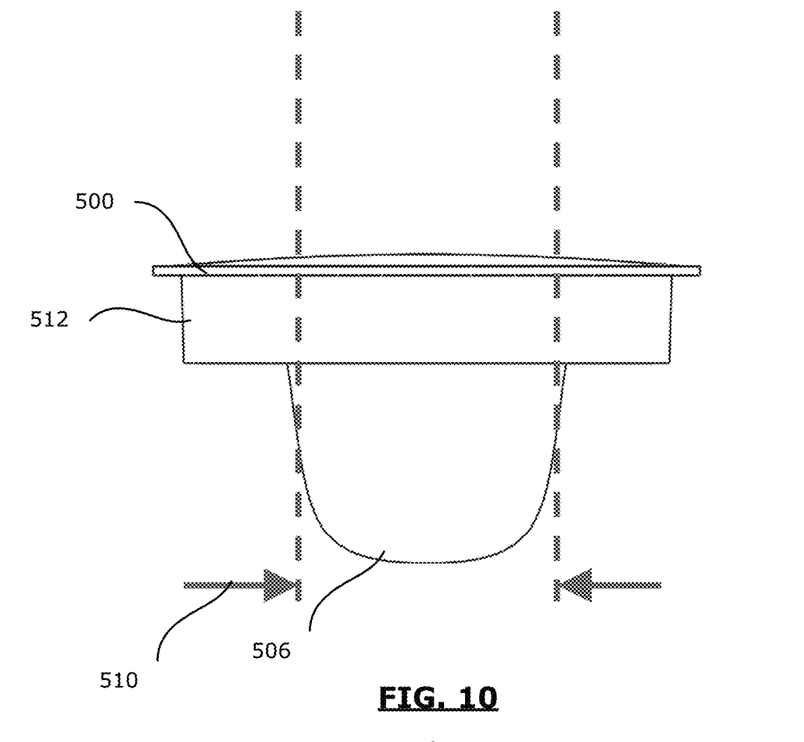
FIG. 10 is a side view of a soft-shell single-serve container according to another embodiment.

Referring now to FIG. 10, a further example container 500 is illustrated. The container 500 has a body portion 506 which has a relatively narrow width 510. The support ring 512 of the container 500 has common exterior dimensions as the support ring 102 of the container 100 of FIG. 1, but the body portion 506 is narrower than the body portion 106 of the container 100 of FIG. 1. More specifically, the cavity which stores the contents of the container 500 is concentrated near the center of the container.

Figure 11:
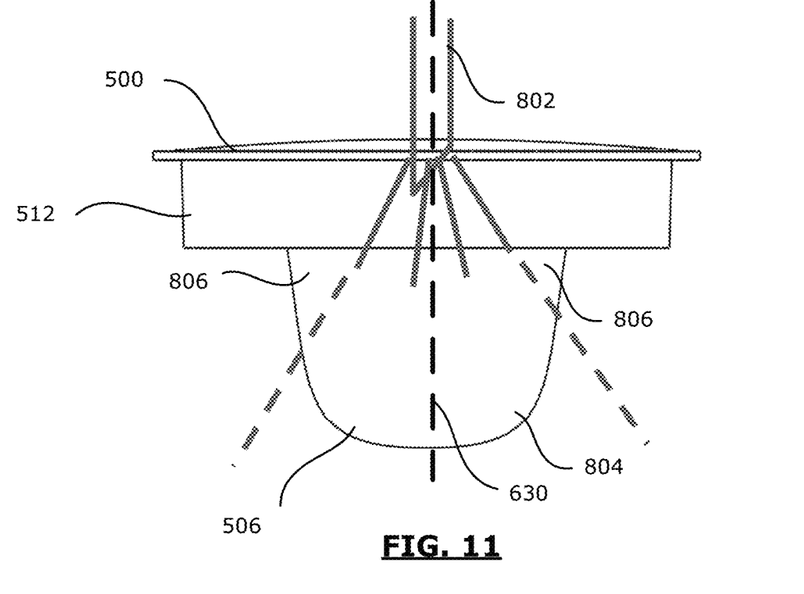
FIG. 11 is a side view of the container of FIG. 10 and a nozzle associated with a brewing machine.
Figure 12:
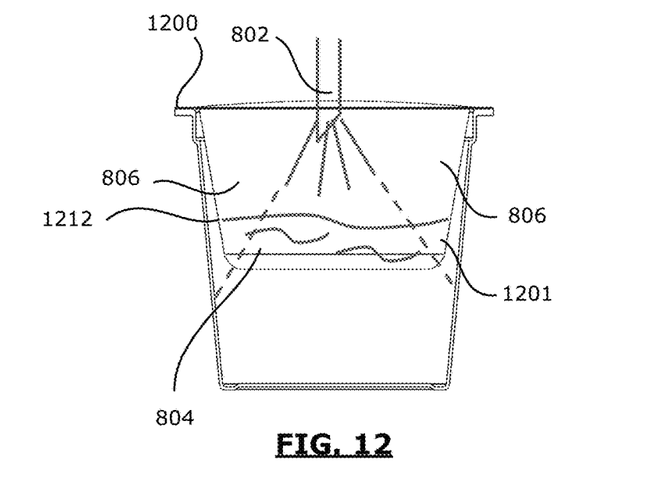
FIG. 12 is a cross sectional view of a hard-shell container and a nozzle associated with a brewing machine.
Figure 13:
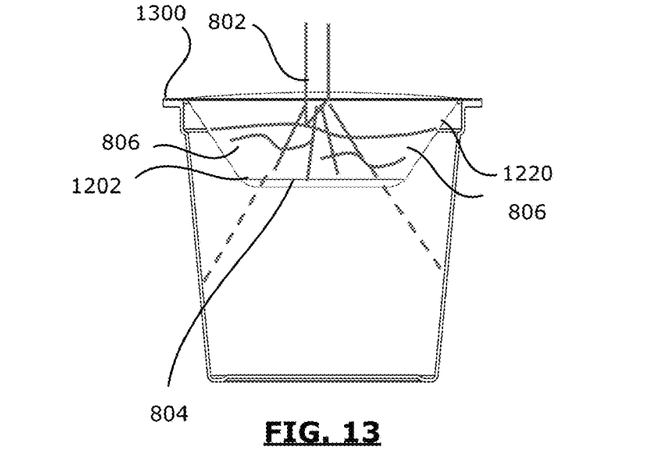
FIG. 13 is a cross sectional view of a hard-shell container and a nozzle associated with a brewing machine.
Figure 14:
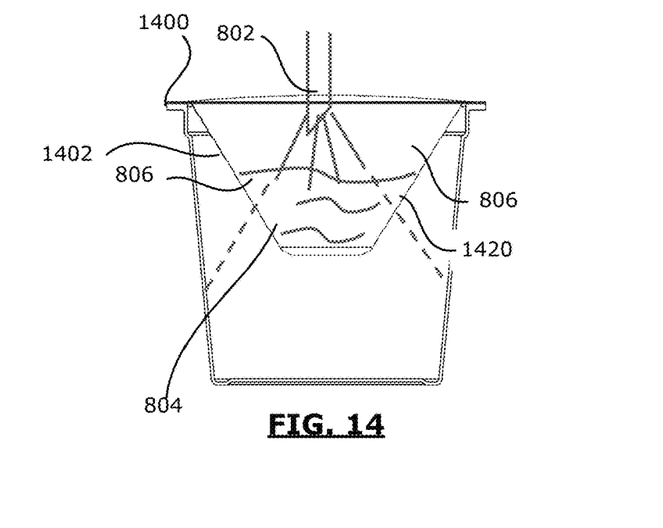
FIG. 14 is a cross sectional view of a hard-shell container and a nozzle associated with a brewing machine.

The wetting effect of this arrangement is shown in FIG. 11. As illustrated in FIG. 11, the proportion of the container's cavity which is within the nozzle spray zone 804 is higher than with the embodiments of FIGS. 8 and 9. In at least some embodiments, the body portion 506 may be oriented so that 80% of the cavity defined by the membrane and the body portion is within the nozzle spray zone 804 (i.e. no more than 20% of the volume of the cavity is within the nozzle spray periphery zone 806).

In some embodiments, at least 95% of the cavity is within 1.4 centimeters of an axis 630 centrally located within the container (this axis 630 is also centrally located with respect to the nozzle 802 when the container is in the brewing machine).

In at least some embodiments, the diameter of the body portion 506 at its top end (which attaches to the support ring) is at least 35% less (or at least 40% less in some other embodiments) than the external diameter of the support ring 512. Thus, even though the support ring may be sized to work with a standard cartridge seat (which is relatively large) for a brewer, the contents of the container are nevertheless concentrated around the nozzle.

In the embodiment of FIG. 11, the body portion 506 is generally shaped as a truncated cone.

Accordingly, FIG. 9 and FIG. 10 (which is also shown in FIG. 11) show two embodiments, each with an internal volume of about 15 mL despite the shape difference (this volume may be varied). The container in FIG. 9 is a flatter format (i.e. shorter) at about 1.6 cm height and an average filter diameter of about 3.5 cm. The single serve container in FIG. 10 has an arrangement more conducive to better wetting for certain spray patterns and having a more centralized formation and containment of the contents. It has a smaller diameter and is taller with a height of approximately 2.8 cm and an average filter diameter of about 2.6 cm. Thus, in at least some embodiments, containers are described where the ratio of the height of the container (or filter) to the average diameter of the filter is greater than 0.6. In some embodiments, this ratio may be greater than 0.8. In some embodiments, this ratio is in the range of 0.6 to 1.3. It will be appreciated that this ratio may be used as a measure of the degree to which the contents of the container are concentrated about the center of the container.

Similar modifications may be made to the filter of a hard-shell single-serve container (e.g. of the type described with respect to FIGS. 4 and 5) to ensure that the contents of the container are wetted.

Referring now to FIG. 12, an example hard-shell single serve container 1200 is illustrated. The hard-shell single serve container 1200 is, in the example illustrated, configured so that the contents 1201 in the filter 1212 do not fill the entire filter. That is, the filter 1212 is relatively deep and is not filled completely to ensure that the contents are wetted. As illustrated, this orientation allows a large portion of the contents of the filter to be within the nozzle spray zone 804. For example, in the embodiment illustrated, the filter is filled to less than 50% of its capacity and most of the contents are within the nozzle spray zone 804. In some embodiments, at least 30% of the cavity defined by the filter 1212 and the membrane may be empty.

Depending on how forcefully the water exits the nozzle, such an orientation may create a splashing effect which causes the contents of the container to splash and possibly stick against the interior wall of the filter or body portion and no longer be within the spray zone. Thus, the orientation of FIG. 12 may not be suited to all applications.

Referring now to FIG. 13, a further example hard-shell single-serve container 1300 is illustrated. In this example, the filter 1202 has a truncated cone shape (similar to the embodiment of FIGS. 4 and 5), but the sidewall 1220 of the filter 1202 is less vertical. For example, in some embodiments, the sidewall has a slope of approximately 60 degrees. In at least some embodiments, the sidewall may have a slope of between 45 and 65 degrees.

In the example of FIG. 13, the single-serve container is filled to capacity or near capacity. That is, the contents of the container occupy almost all of the space in the cavity defined by the membrane and the filter. In at least some embodiments, the contents of the container occupy at least 95% of the cavity's volume.

Referring now to FIG. 14, a further example single-serve container 1400 is illustrated. This example container combines the features of the container of FIG. 12 with those of the container 1300 of FIG. 13. That is, the cavity is not completely filled (e.g. is filled to less than 60% capacity) and the filter 1402 has a sidewall 1420 having a slope between 45 and 65 degrees. As can be seen in FIG. 14, this orientation causes a large portion of the contents of the container to be within the nozzle spray zone 804.

A container of a type described herein (and containing ingredients of the type described herein) may, in at least some embodiments, be used according to one or more of the following methods to brew a beverage. First, the container is inserted into a single-serve brewing machine. For example, the container may be placed on a cartridge seat of the brewing machine. The membrane of the container is pierced by the brewing machine, typically when the brewing machine is closed. More particularly, a needle pierces the membrane and enters the interior space defined by the container's body portion and membrane. Depending on the container's configuration (e.g., whether it is a hard shell container or a soft shell container), the bottom of the container may also be pierced to create an exit port for a brewed beverage. An instruction is then input into the brewing machine to instruct the brewing machine to initiate a brew cycle. This instruction may, for example, be input to the brewing machine using a button or other input mechanism associated with the machine. The instruction is received at the brewing machine in the form of a signal (e.g. an electrical signal).

After the needle pierces the brewing machine and in response to receiving the instruction to initiate the brewing cycle, water is injected into the container from the needle. This water mixes with the processed *cannabis* product and the extraction agent and creates a beverage which includes active cannabinoids. The brewed beverage exits the container either through the permeable body portion (i.e., if the container is a soft shell container) or through the exit port created by piercing the container (i.e., if the container is a hard shell container).

After the brew cycle has completed, the brewed beverage may then be consumed.

Modifications apart from those described above may be made to the single-serve containers in other embodiments to draw the contents to within the nozzle spray zone and the specific modifications may depend on depth of the nozzle, velocity of water expelled from the nozzle, and the diameter of the nozzle, for example.

It will be appreciated that the techniques described herein may be used to create a packaged beverage product which may be delivered in another form, apart from the single serve container described above. For example, in some embodiments, *cannabis* processed (e.g., decarboxylated and/or pulverized) according to the techniques described above may be packaged with other ingredients of the types described above (e.g. the extraction agent and/or flavoring agent) for creating a steeped or brewed beverage. For example, in some embodiments, such contents may be packaged in a tea bag. In some embodiments, the contents may be sold in a blended form (e.g. the processed *cannabis*, extraction agent and, in some embodiments, flavoring agent) may be blended and sold. Such contents could then be added to a tea infuser, filter brewing machine, percolator, or French press, for example, to create a beverage. For example, when a tea infuser is used the tea infuser will be placed in hot or cold water.

The various embodiments presented above are merely examples. Variations of the innovations described herein will be apparent to persons of ordinary skill in the art, such variations being within the intended scope of the present application. In particular, features from one or more of the above-described example embodiments may be selected to create alternative example embodiments including a sub- combination of features which may not be explicitly described above. In addition, features from one or more of the above-described example embodiments may be selected and combined to create alternative example embodiments including a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method of preparing a packaged beverage product, the method comprising:
    processing *cannabis* by heating the *cannabis* to decarboxylate the *cannabis*;
    adding the processed *cannabis* to the packaged beverage product;
    adding, to the packaged beverage product, a food-based extraction agent, wherein the extraction agent is a powder and is solid at room temperature; and
    sealing the packaged beverage product.

2. The method of claim 1, wherein the extraction agent is selected from the group consisting of milk powder, powdered dairy creamer, powdered non-dairy creamer, cocoa powder, chocolate powder, powdered coconut flakes, coconut flour, flax meal powder, *quinoa* flour, and almond flour.

3. The method of claim 1, further comprising, prior to sealing:
    adding, to the packaged beverage product, a flavoring agent.

4. The method of claim 3, wherein the flavoring agent is selected from the group consisting of:
    tea, coffee or chocolate, latte and cappuccino.

5. The method of claim 1, further comprising:
    pulverizing the *cannabis*.

6. The method of claim 5, wherein pulverizing comprises pulverizing the *cannabis* to a particle size of 2 millimeters or less.

7. The method of claim 5, wherein pulverizing comprises pulverizing the *cannabis* to a particle size of 1 millimeter or less.

8. The method of claim 5, further comprising, after pulverizing, filtering the pulverized *cannabis* to separate *cannabis* having a desired particle size.

9. The method of claim 1, wherein a particle size of the processed *cannabis* is within 15% of the particle size of the extraction agent.

10. The method of claim 1, wherein adding the processed *cannabis* to the packaged beverage product comprises adding the processed *cannabis* to the packaged beverage product using a filling head which dispenses a predetermined amount of the processed *cannabis* to the packaged beverage product.

11. The method of claim 1, wherein the packaged beverage product is a tea bag.

12. The method of claim 1, wherein the extraction agent is a lipid-rich extraction agent.

* * * * *